United States Patent
Dawson et al.

(10) Patent No.: US 9,456,947 B2
(45) Date of Patent: Oct. 4, 2016

(54) HEAD POSITIONING DEVICE

(71) Applicant: Vision RT Limited, London (GB)

(72) Inventors: Dana M Dawson, Troy, NY (US);
Umar M Baharom, Troy, NY (US);
Martin Allen, London (GB); Norman R Smith, London (GB)

(73) Assignee: VISION RT LIMITED, London (GB)

( * ) Notice: Subject to any disclaimer, the term of this patent is extended or adjusted under 35 U.S.C. 154(b) by 604 days.

(21) Appl. No.: 13/962,543

(22) Filed: Aug. 8, 2013

(65) Prior Publication Data
US 2015/0045676 A1  Feb. 12, 2015

(51) Int. Cl.
| A61G 13/12 | (2006.01) |
| A61B 6/04 | (2006.01) |
| A61G 13/04 | (2006.01) |
| A61G 13/08 | (2006.01) |
| A61B 5/00 | (2006.01) |
| A61B 5/11 | (2006.01) |
| A61N 5/10 | (2006.01) |
| A61B 6/00 | (2006.01) |

(52) U.S. Cl.
CPC .......... *A61G 13/121* (2013.01); *A61B 5/0077* (2013.01); *A61B 5/1128* (2013.01); *A61B 5/4836* (2013.01); *A61B 5/704* (2013.01); *A61B 6/0492* (2013.01); *A61G 13/04* (2013.01); *A61G 13/08* (2013.01); *A61N 5/1049* (2013.01); *A61B 6/501* (2013.01); *A61G 2210/50* (2013.01); *A61N 2005/1059* (2013.01); *A61N 2005/1097* (2013.01)

(58) Field of Classification Search
CPC .......... A61G 7/05; A61G 7/07; A61G 7/072; A61G 7/1084; A61G 13/10; A61G 13/12; A61G 13/121; A61B 6/00; A61B 6/04; A61B 6/0407; A61B 6/501

USPC .................. 5/622, 621, 636, 640, 601, 600; 378/208, 209
See application file for complete search history.

(56) References Cited

U.S. PATENT DOCUMENTS

| 3,188,079 | A | * | 6/1965 | Boetcker | A61G 13/12 |
| | | | | | 297/391 |
| 4,736,736 | A | * | 4/1988 | Moers | A61H 1/0218 |
| | | | | | 5/637 |
| 5,013,018 | A | * | 5/1991 | Sicek | A61B 6/0457 |
| | | | | | 378/209 |
| 6,094,760 | A | * | 8/2000 | Nonaka | A61B 6/0457 |
| | | | | | 5/600 |
| 6,138,302 | A | * | 10/2000 | Sashin | A61B 6/0421 |
| | | | | | 5/600 |

(Continued)

FOREIGN PATENT DOCUMENTS

| WO | 00/27331 A2 | 5/2000 |
| WO | 03/061477 A1 | 7/2003 |
| WO | 2004/032781 A1 | 4/2004 |

*Primary Examiner* — Robert G Santos
(74) *Attorney, Agent, or Firm* — Kenealy Vaidya LLP

(57) ABSTRACT

A head positioning device for use in radio therapy is described for positioning a patient's head. The head positioning device comprises a head plate for supporting a patient's head; a base plate for connection to a mechanical couch; and a head plate adjustment assembly connecting the head plate to the base plate wherein the head plate adjustment assembly is arranged to vary the relative pitch, yaw and roll of the head plate relative to the base plate. The head positioning device is arranged to be attached to a mechanical couch with the head plate and the head plate adjustment assembly cantilevered off the end of the couch and the head plate adjustment assembly suspended beneath the head plate and the base plate.

10 Claims, 7 Drawing Sheets

(56) References Cited

U.S. PATENT DOCUMENTS

| | | | |
|---|---|---|---|
| 7,181,792 B2 * | 2/2007 | Nakamura | A61B 6/04 378/209 |
| 7,348,974 B2 | 3/2008 | Smith et al. | |
| 7,882,583 B2 * | 2/2011 | Skripps | A61G 13/04 5/621 |
| 7,889,906 B2 | 2/2011 | Smith et al. | |
| 8,135,201 B2 | 3/2012 | Smith et al. | |
| 8,234,731 B2 * | 8/2012 | Skripps | A61G 13/04 5/621 |
| 8,485,195 B2 * | 7/2013 | River | A61H 1/0296 128/830 |
| 2005/0028280 A1 * | 2/2005 | Nakamura | A61B 6/04 5/601 |
| 2006/0253985 A1 * | 11/2006 | Skripps | A61G 13/04 5/622 |
| 2007/0032795 A1 * | 2/2007 | Schloesser | A61N 5/1049 606/130 |
| 2009/0187112 A1 | 7/2009 | Meir et al. | |
| 2009/0272835 A1 * | 11/2009 | Benvenuti | B65H 19/2269 242/521 |
| 2011/0131727 A1 * | 6/2011 | Skripps | A61G 13/04 5/622 |
| 2012/0006336 A1 | 1/2012 | Meir et al. | |
| 2015/0045676 A1 * | 2/2015 | Dawson | A61G 13/121 600/476 |
| 2015/0202073 A1 * | 7/2015 | Zacharopoulos | A61F 5/3707 128/845 |

* cited by examiner

HEAD POSITIONING DEVICE

FIELD OF THE INVENTION

The present invention concerns a device for positioning a patient's head. In particular, embodiments of the present invention concern devices for positioning the head and neck of a patient during radiotherapy or similar treatments.

BACKGROUND TO THE INVENTION

Radiotherapy consists of projecting onto a predetermined region of a patient's body, a radiation beam so as to destroy or eliminate tumors existing therein. Such treatment is usually carried out periodically and repeatedly. At each medical intervention, the radiation source must be positioned with respect to the patient in order to irradiate the selected region with the highest possible accuracy to avoid radiating adjacent tissue on which radiation beams would be harmful.

A fundamental problem with radiotherapy is the need to position the patient in the same position, when obtaining diagnostic images and each of the subsequent times when radiation is applied to the patient's body. It is to that end that Vision RT have developed an image processing system for monitoring and positioning patients described in U.S. Pat. No. 8,135,201, U.S. Pat. No. 7,889,906, U.S. Pat. No. 7,348,974, and pending US patent applications US2012/0006336 and US2009/0187112 all of which are hereby incorporated by reference.

In use, in the Vision RT system images of a patient on a mechanical couch are obtained by a set of stereoscopic cameras which are then processed to generate a 3D wire mesh model of the surface of a patient being monitored. This 3D wire mesh model is compared with a reference surface created during treatment planning. The relative positioning of the model and the reference surface is compared and used to generate instructions for the mechanical couch to be moved vertically, laterally and rotationally so as to match the surfaces and hence locate the patient reliably in the same location relative to the iso-center of a treatment apparatus. Subsequently during treatment, the position of a patient is continually monitored and if for any reason the patient moves or repositions themselves, this can be detected and if necessary treatment can be halted and the patient repositioned.

Particularly, where the radiotherapy is used to treat cancers inside the cranium, the destruction and damage of nearby healthy tissue can result in severe side effects due to the presence of many critical structures and organs in that part of the body. For this reason, it is very important that radiation is targeted as far as possible so as to destroy only the cancerous cells whilst leaving other nearby structures intact.

Devices immobilizing the position of a patient's head and neck are used to improve the accuracy and reproducibility of positioning the head and neck in medical diagnostic and treatment procedures. Examples of these are described in PCT patent applications WO00/27331, WO03/061477 and WO04/032781 and Vision RT's own pending US patent application US2012/006336. Typically such immobilization devices comprise a cushion and face mask made out of a thermoplastic material which is heated prior to an initial treatment session. The patient lies with their head on the cushion a mask is then molded to a patient's head by being placed over the patient's face and then allowed to set. The resultant rigid mask encloses a patient's head and thus restricts movement and allows a patient to be placed into a fixed position for each treatment session.

Given the importance of accurate positioning for radiotherapy and particularly radiotherapy to treat cancers of the head and neck, it is highly desirable to position a patient with ever greater accuracy. Typically, a mechanical couch is only able to vary the position of a patient, vertically, laterally and rotationally. Although, such adjustments are normally sufficient for most treatments, in the case of cancers of the head and neck, a patient can naturally vary the inclination of their head which adds additional complications to maintaining accurate patient positioning.

Further, it is difficult to make fine adjustments to the positioning of a patient using a mechanical couch. When a patient is lying on a mechanical couch, repositioning a patient requires moving both the patient and the mechanical couch to a new location. This means moving the entire weight of both the patient and the mechanical couch itself. Additionally, most mechanical couches which are able to rotate about an axis of rotation, rotate about an axis which is aligned with a presumed position of the iso-center of a treatment apparatus rather than being able to rotate about the iso-center itself. As a result, almost invariably, some small translations relative to the iso-center are introduced whenever a rotational movement is made which then have to be corrected for separately. This complicates positioning a patient and makes very small (e.g. sub millimeter) patient positioning very challenging and time consuming.

It is therefore desirable to provide a patient positioning system which can help to locate a patient's head in a fixed position to a high level of accuracy and which works with the natural range of movement that is possible for a patient.

SUMMARY OF THE INVENTION

In accordance with one aspect of the present invention there is provided a patient positioning device which is adapted to be connected to a mechanical couch which enables the positioning of a patient's head to be adjusted. The patient positioning device is arranged to be able to adjust the positioning of a patient's head in pitch, yaw and roll where the axes of adjustment substantially correspond to the axes of movement of a patient' neck. The patient positioning device therefore provides an additional level of fine adjustment for the positioning of a patient which supplements the positioning which can be achieved with positioning using a mechanical couch and achieves this through movements which correspond with axes of movement of a patient's neck. When combined with a patient monitoring system this enables very high accuracy of patient positioning to be achieved in a way which minimizes discomfort for a patient.

In embodiments of the present invention, the patient positioning device may be arranged to be attached to a mechanical couch with a portion of the device cantilevered off the end of a mechanical couch. When in such a position, the adjustment mechanism of the device may be suspended beneath the patient positioning system adjacent the end of the couch.

Preferably the adjustment mechanism includes three knobs one each for adjusting the pitch, yaw and roll of the head of a patient attached to a head plate of the patient positioning system via a face mask. Preferably the gearing of the adjustment mechanism is such that the rotation of the pitch, yaw and roll adjustment knobs generates similar variations in rotation. Further, preferably the adjustment mechanism is able to adjust the rotation of a patient's head by about ±3° about each axis of movement, such that the range of possible movements of the adjustment device does not exceed a comfortable range for a patient.

In some embodiments, the patient positioning device may additionally be able to make adjustments to the lateral and vertical positioning of a patient's head, thereby providing an additional degree of flexibility in the positioning of a patient.

BRIEF DESCRIPTION OF THE DRAWINGS

Further aspects and embodiments of the present invention will become apparent with reference to the following description and accompanying drawings in which.

DETAILED DESCRIPTION OF THE PREFERRED EMBODIMENTS

Figure 1:
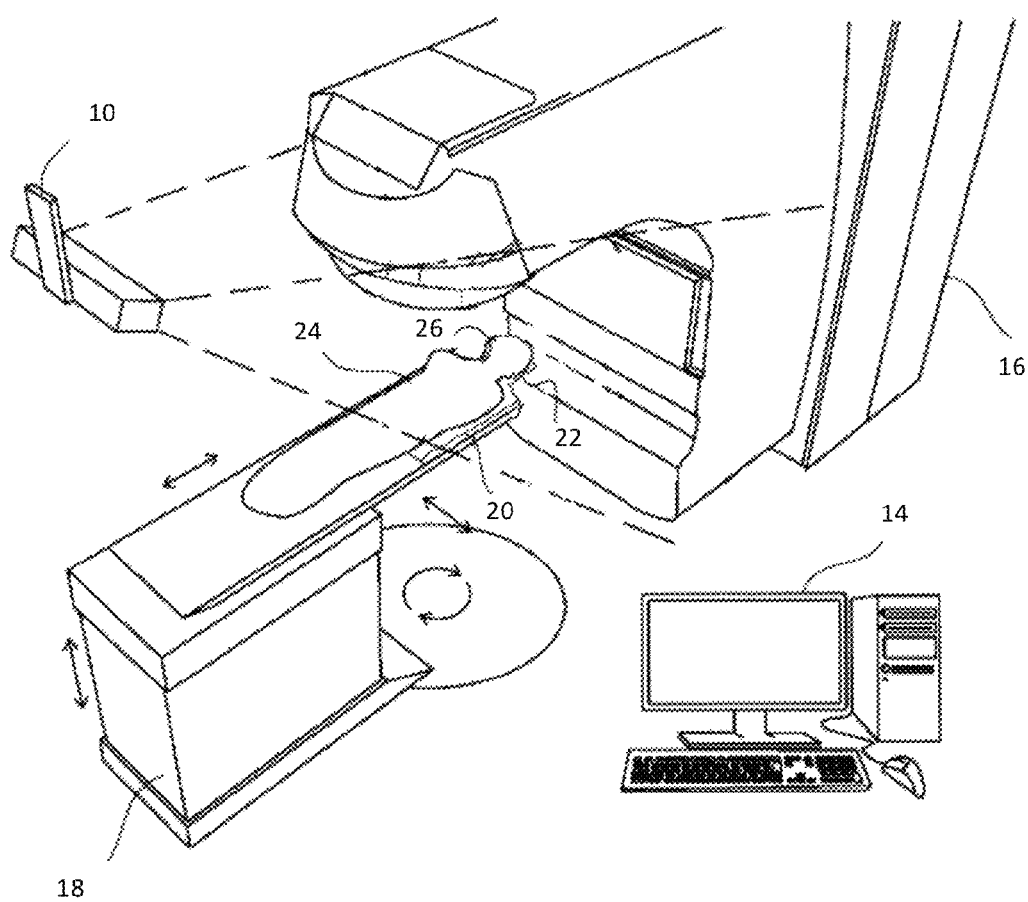
FIG. 1 is a schematic perspective view of a treatment system including a head positioning device in accordance with a first embodiment of the present invention.

FIG. 1 is a schematic perspective view of a treatment system including a head adjustment device in accordance with a first embodiment of the present invention. The treatment system includes a set of stereoscopic cameras 10 that are connected by wiring (not shown) to a computer 14. The computer 14 is also connected to a treatment apparatus 16 such as a linear accelerator for applying radiotherapy. A mechanical couch 18 is provided as part of the treatment apparatus. The treatment apparatus 16 and the mechanical couch 18 are arranged such that, under the control of the computer 14, the relative positions of the mechanical couch 18 and the treatment apparatus 16 may be varied, laterally, vertically, longitudinally and rotationally as is indicated in the figure by the arrows adjacent the couch.

In use, a head positioning device 20 is attached to the surface of the mechanical couch 18 with a head plate 22 cantilevered off the end of the mechanical couch 18. The patient 24 then lies on the mechanical couch 18 with their head 26 supported on a molded cushion resting on the head plate 22. The patient 24 is then held in place on the mechanical couch 18 by a molded face mask being placed over their head 26 and attached to the head plate 22 or by having an invasive head ring attached to their head and attached to the head plate 22.

Images of the patient are then obtained by the stereoscopic cameras 10. These images are passed to and processed by the computer 14 which proceeds to generate a 3D wire mesh computer model of the surface of the patient's head 26. The generated 3D wire mesh computer model is compared with a reference surface for the patient generated at the planning stage of the treatment process. The computer 14 then determines a rigid transformation for matching the modeled surface of the patient with the reference surface. This transformation is then sent to the mechanical couch 18 which repositions itself laterally, vertically, longitudinally and rotationally to match the surface of the patient's head 26 with the reference surface as best as it can.

Having used the matching of the modeled surface of the patient 24 and the reference surface to position the mechanical couch 18, the stereoscopic cameras 10 obtain further images of the patient 24. These images are processed by the computer 14 which determines any further fine transformations required to match the surface of the patients head 26 with a stored reference surface. Fine adjustments for the pitch, roll and yaw of the head plate 22 of the head positioning device can then be made. These adjustments can continue to be made iteratively with feedback received from the computer 14 and stereoscopic cameras 10 until the surface of the head 26 of the patient 24 best matches the reference surface obtained during planning. When differences between the two surfaces have been minimized, the treatment apparatus 16 can be used to apply radiation to the patient 24 in the knowledge that the patient's head 26 has been reliably positioned in the position which corresponds to the stored reference surface.

Figure 2:
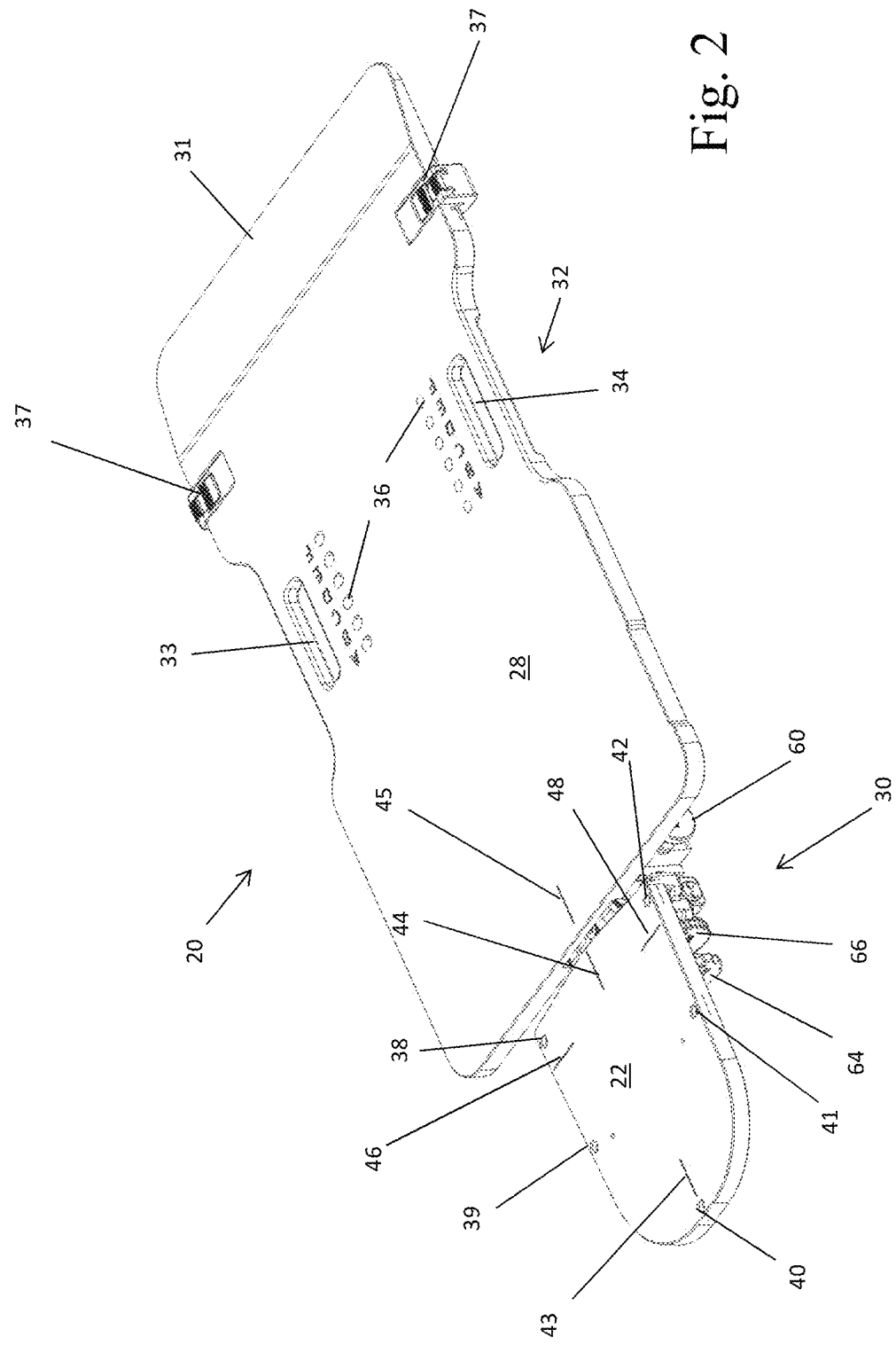
FIG. 2 is a perspective view of the head positioning device of FIG. 1.
Figure 3:
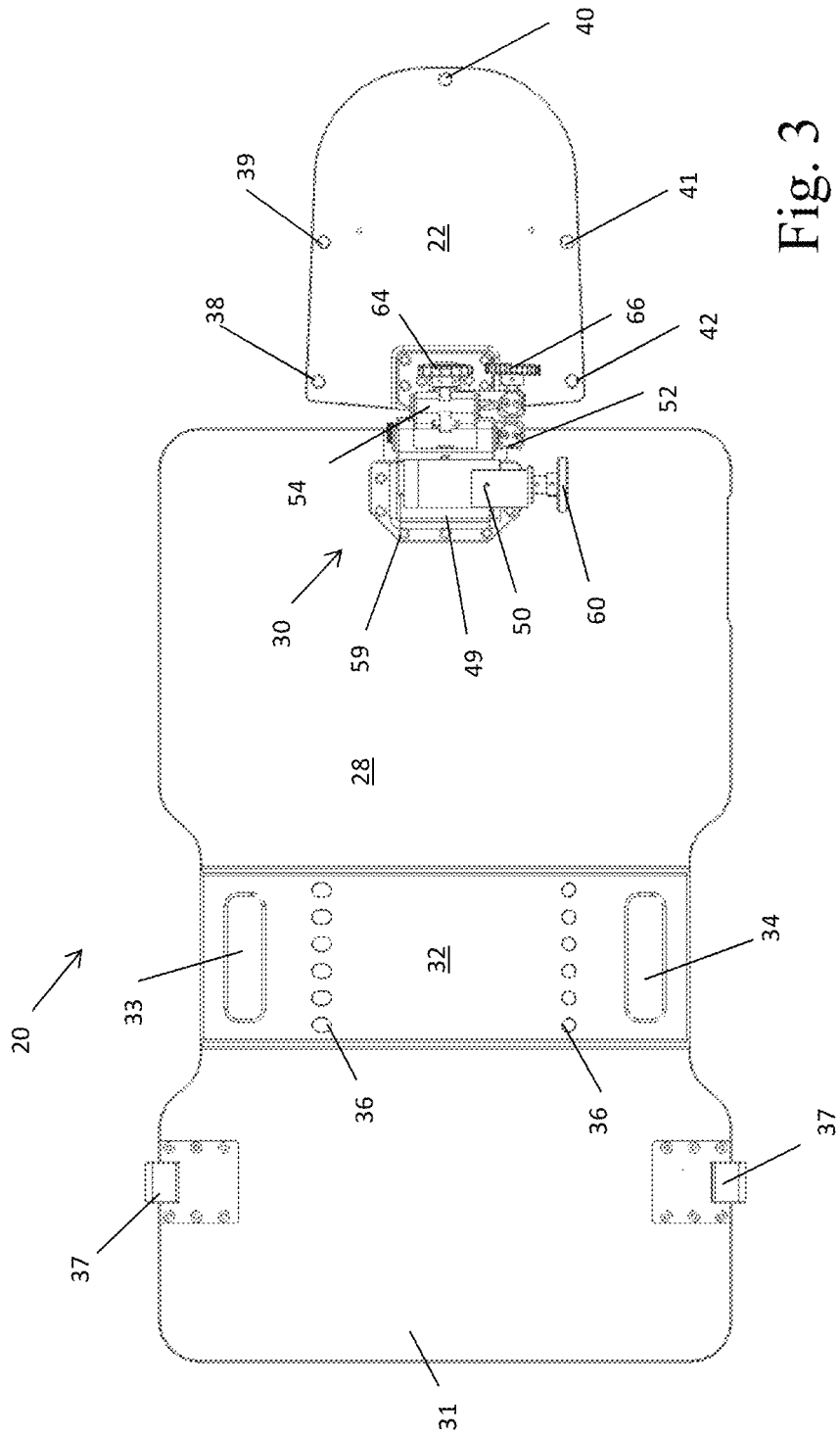
FIG. 3 is an underneath plan view of the head positioning device of FIG. 1.

FIG. 2 is a perspective view of the head positioning device 20 of FIG. 1 and FIG. 3 is an underneath plan view of the device 20.

As can be seen in the figures, the head positioning device 20 comprises a base plate 28 and a head plate 22 which are connected together via a head plate adjustment assembly 30. The head plate adjustment assembly 30 is suspended beneath the base plate 28 and the head plate 22 and, as will be described in greater detail later, in this embodiment is able to adjust the relative, pitch, yaw and roll of the head plate 22 relative to the base plate 28.

In this embodiment, the base plate 28 is substantially rectangular in shape, being approximately 90 cm in length and having a width of approximately 55 cm at it greatest extent. The thickness of the baseplate 28 is uniform except for a portion 31 of the base plate remote from the head plate 22 where the base plate 28 is tapered to reduce in thickness so that a patient 20 can comfortably lie on the base plate 28 when it is attached to a mechanical couch 18 and a central section 32 of the base plate 28 which is reduced in thickness. In this embodiment the long edges of the base plate 28 are scalloped so as to have indentations approximately a third of the way along the edge. These indentations are such to expose a portion of the surface of a mechanical couch 18 when the base plate 28 is placed on the surface of the mechanical couch 18 thereby exposing attachment points for other apparatus which may be used in conjunction with the treatment system.

Adjacent to the indentations provided by the scalloped edges are a pair of slots 33, 34 which are suitable for use as hand holds when placing the base plate 28 on the surface of the mechanical couch 18 and an indexing system comprising a series of indexing holes 36 next to marks on the upper surface which are visible in FIG. 2 and comprise the letters A-F. In use, when attaching the head positioning device 20 to the mechanical couch 18, a bar is provided that extends across the width of the mechanical couch 18 at a fixed location with a pair of pins protruding from the surface of the bar. The position and size of the pins are such that when placed on the surface of the mechanical couch 18, the pins will protrude through a pair of indexing holes with the bar visible through the slots 33, 34. A clamping mechanism 37 is then provided next to the tapered portion 31 of the base plate 28 to fix the base plate 28 in position. Although a single clamping mechanism 37 is shown for attaching a base plate 28 to the surface of a mechanical couch 18, different clamping mechanisms could be used to attach a base plate 28 to different styles of mechanical couch 18. More specifically, portions of the clamping mechanism 37 could be removable so that different shaped clamps could be attached to the base plate 28 so that the base plate 28 could be adapted to be clamped using a clamping mechanism specifically shaped to clamp to a particular design of mechanical couch 18.

The provision of the slots 33, 34 and indexing holes 36 enables the base plate to be fixed onto the mechanical couch 18 at one of a limited number of fixed locations with the identity of the marks through which the pins protrude and the visible position of the bar through the slots 33, 34 providing a visible indication of which of the attachment points has been used. At the same time the central section 32 of the base plate 28 with reduced thickness ensures that the base plate can be placed on the surface of the mechanical couch 18 whilst extending above and over the bar.

The head plate 22 in this embodiment is broadly rectangular but with very slightly tapered sides and a rounded semi-circular end remote from the base plate 28. At the periphery of the head plate 22, there are five holes 38-42 which provide attachment points for attaching a face mask or an invasive head ring to the head plate 22. Two of these attachment holes 38, 42 are in the corners of the head plate 22 adjacent the base plate 28, two attachment holes 39, 41 are provided half way along the long edges of the head plate 22 and one hole is provided at the crown of the curved section of the head plate 22 remote from the base plate 28.

A pair of center markings 43, 44 are provided on the upper surface of the head plate 22. These markings can be visually aligned with a third marking 45 in the middle of the base plate 28 to confirm that the head plate 22 is centered. In typical treatment rooms this is further facilitated by the presence of lasers arranged to project light to identify the iso-center of the treatment apparatus 16 which will typically be aligned with the center of the mechanical couch 18 when the mechanical couch 18 is in a zeroed position. Thus in this position the co-incidence of the laser light with the center markings 43-45 when the mechanical couch 18 is aligned with the iso-center can provide a visual confirmation that the couch 18 and the head plate 22 are correctly positioned with the yaw adjustment of the head plate 22 zeroed.

In addition to the center markings 43, 44, a pair of end markings 46, 48 is also provided on the surface of the head plate. These markings 46, 48 are positioned close to the edge of the head plate 22 nearest the base plate 28 and identify the portion of the head plate 22 beneath which the head plate adjustment assembly 30 protrudes. The purpose of these markings is to provide a visual indication of the portion of the head plate where treatment or imaging radiation should not be applied. This is because in practice, the presence of other objects such as the protruding portion of the head plate adjustment assembly 30 can have an impact on the delivery of the radiation beam, either adsorbing or deflecting portions of the beam, and therefore reducing the accuracy of treatment or interfering with the imaging of a patient. Thus the end markings 46, 48 in this embodiment identify a portion of the apparatus where radiation should not be applied.

Figure 4:
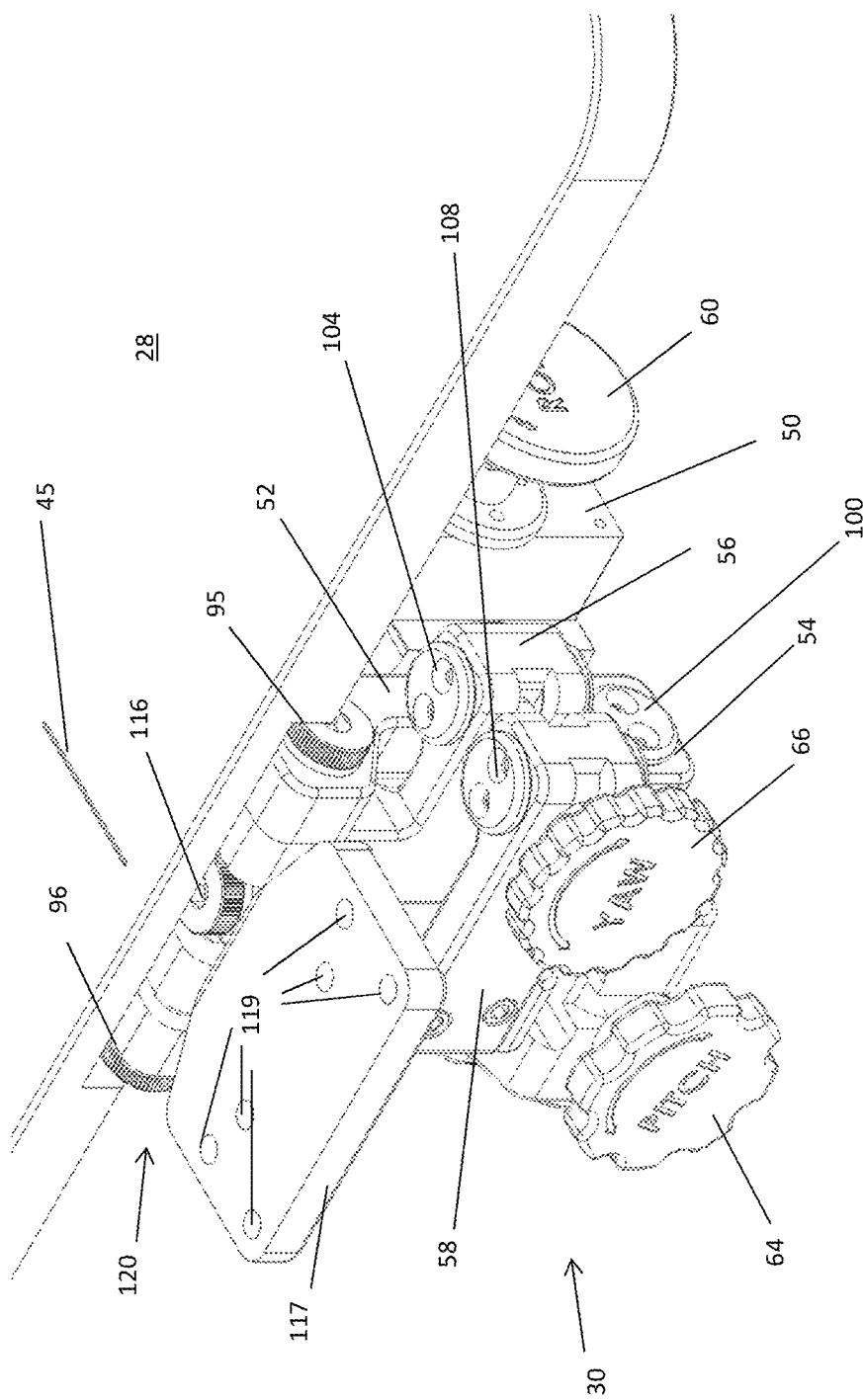
FIG. 4 is a close up perspective view of the head plate adjustment assembly of the head positioning device of FIG. 2 in the absence of a head plate.
Figure 5:
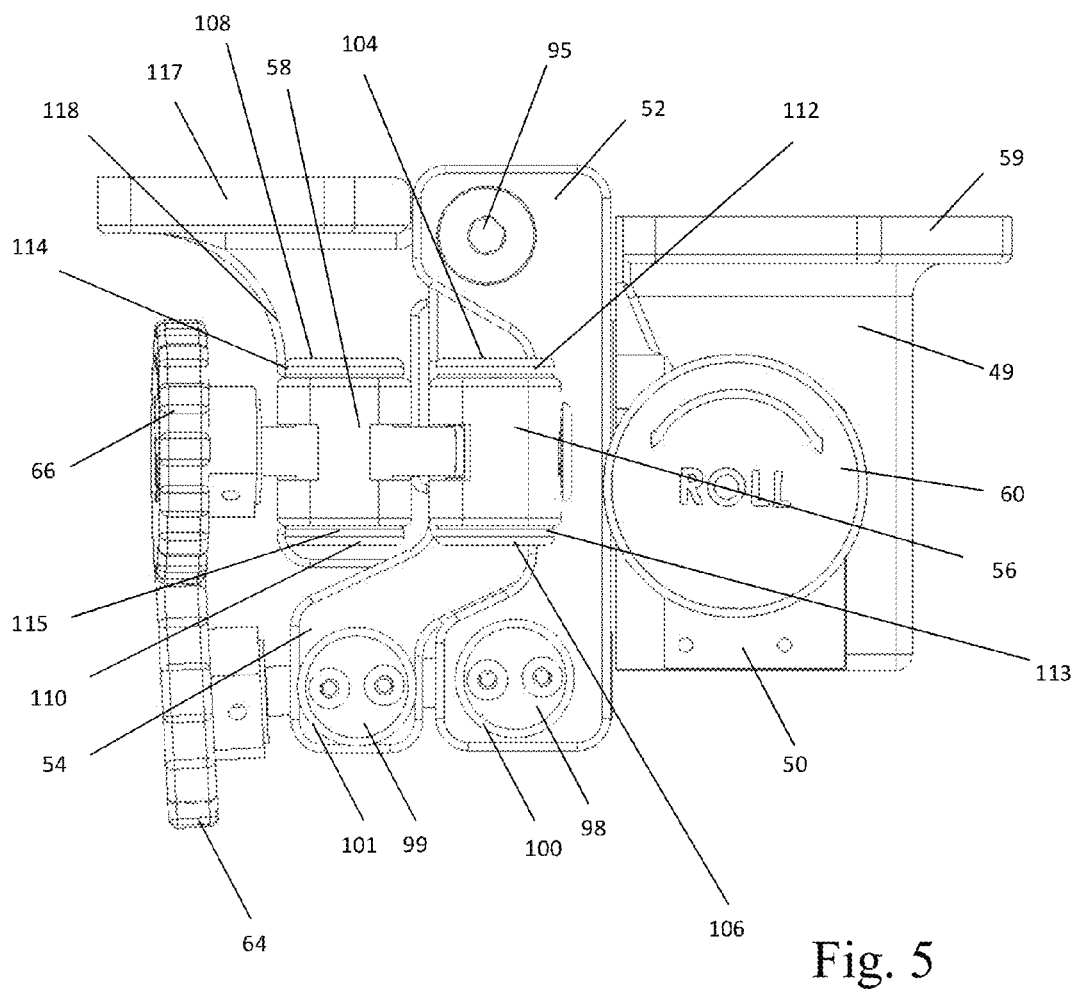
FIG. 5 is a side view of the head plate adjustment assembly of FIG. 4.

FIGS. 4 and 5 are each a close up perspective view of the head plate adjustment assembly 30 of the head positioning device 20 in the absence of a head plate 22 and a side view of the head plate adjustment assembly 30 in the absence of both the base plate 28 and the head plate 22. The head plate adjustment assembly 30 provides a connection between the base plate 28 and the head plate 22 such that the pitch, yaw and roll of the head 26 of a patient 24 can be adjusted with the axes of adjustment corresponding to the axes of movement of a patient's neck when the patient lies on the base plate 28 with their head encased in a face mask or invasive head ring attached to the head plate 22. To achieve this, as can best be seen in FIG. 5, the head plate adjustment assembly 30 comprises: an adapter bracket 49, a rotary stage 50, a pitch bracket 52, and a pitch adjustment arm 54, an inner yaw adjustment arm 56, and outer yaw adjustment arm 58.

The adapter bracket 49 is suspended beneath the base plate 28 with the portion of the adapter bracket 49 immediately beneath the base plate 28 forming a base plate support 59 which is attached to the underside of the base plate 28 by a set of screws (visible in FIG. 3). The rotary stage 50 is housed within a lower portion of the adapter bracket 49 remote from the base plate support 59. The rotary stage 50 is controlled by a roll adjustment knob 60. When the roll adjustment knob 60 is rotated this causes a central portion of the rotary stage 50 attached to the pitch bracket 52 to rotate about an axis extending through the center of the rotary stage parallel with the surface of the base plate 28. This in turn causes the pitch bracket 52 which is attached to the rotary stage 50 to rotate which in turn causes the remainder of the head plate adjustment assembly 30 and the attached head plate 28 to make a corresponding rotation. In this embodiment the rotary stage 50 can be constructed from a conventional photographic rotary stage to which is added gearing so that the rotation of the roll adjustment knob 60 of the rotary stage 50 causes a similar amount of rotation as adjustment of the pitch and yaw adjustment knobs 64, 66 to cause corresponding adjustments in pitch and yaw.

Figure 6:
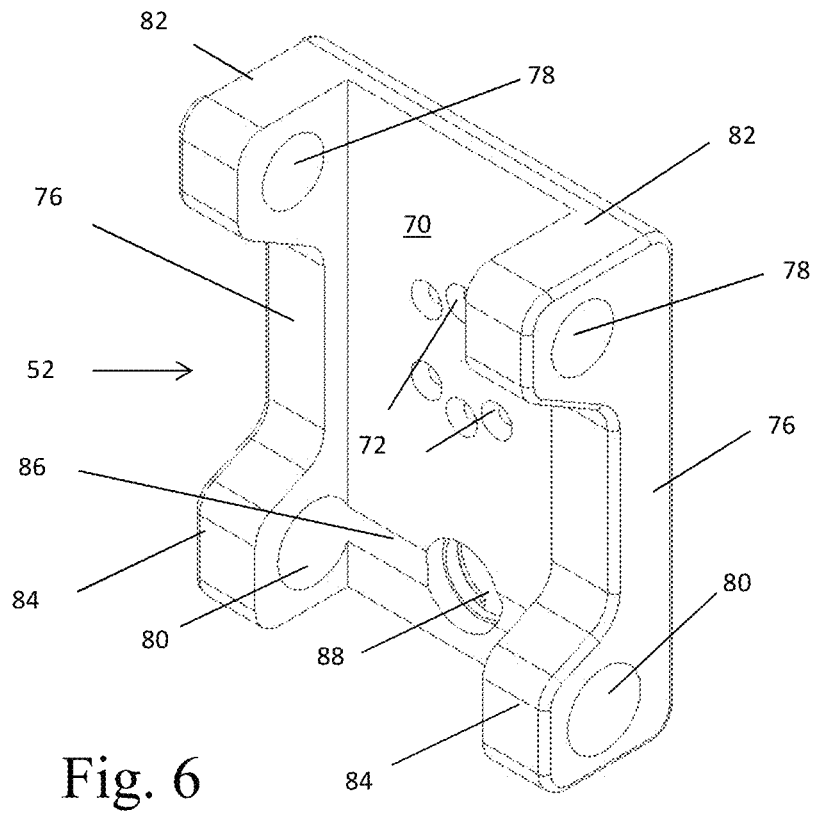
FIG. 6 is a perspective view of the pitch bracket of the head plate adjustment assembly of FIG. 4.

FIG. 6 is a perspective view of the pitch bracket 52 of the head plate adjustment assembly 30. The pitch bracket comprises a back plate 70 which is attached to the rotary stage 50 by screws passing through a set of screw holes 72 in the center of the back plate 70 so that the pitch bracket 52 is caused to rotate when the roll adjustment knob 60 is rotated.

Two U-shaped projections 76 extend away from the surface of the back plate 70 at the edges of the back plate 70. At the ends of the arms of the U shaped projections 76 are a pair of holes 78, 80. The circumference of the holes 78 in the upper arms 82 provide a pivot hole for containing a pivot about which the pitch adjustment arm 54 can rotate, thereby adjusting the relative pitch between the pitch adjustment arm 54 and the plane of the back plate 70 of the pitch bracket 52 attached to the rotary stage 50. The holes 80 in the lower arms 84 are arranged to receive and act as a seat for a barrel mounted on the screw thread of a pitch adjustment knob 64.

In this embodiment, the circumference of the holes 80 in the lower arms 84 are larger than the circumference of the holes 78 in the upper arms 82 and a recess 86 is provided in the back plate 70 which is curved to correspond with the curve of the holes 80. In this way when the ends of a barrel are accommodated within the holes 80 of the lower arms 84, a portion of the barrel is contained within the recess 86 which acts to support the barrel and the weight of the remainder of the head plate adjustment assembly 30. In this embodiment a hole 88 is provided in the center of the recess 86 which allows a screw thread associated with the pitch adjustment knob 64 to extend through the back plate 70 of the pitch bracket 52.

Figure 7:
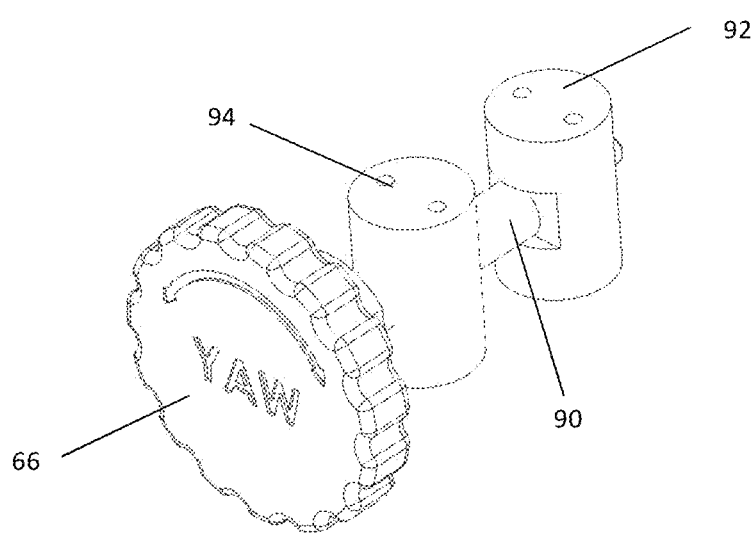
FIG. 7 is a perspective view of the yaw adjustment knob and yaw adjustment barrels of the head plate adjustment assembly of FIG. 4.

FIG. 7 is a perspective view of the yaw adjustment knob 66 of the head plate adjustment assembly 30. A screw thread 90 is attached to the yaw adjustment knob 66 and a pair of yaw adjustment barrels 92, 94 are mounted on the screw thread 90.

The yaw adjustment barrel 92 remote from the yaw adjustment knob 66 is at a fixed location on the screw thread 90. In contrast, the yaw adjustment barrel 94 closer to the yaw adjustment knob 66 is mounted on the screw thread 90 such that as the yaw adjustment knob 66 is rotated, the barrel 94 moves along the screw thread 94. Thus in this way, since the distance between the yaw adjustment knob 66 and the yaw adjustment barrel 92 remote from the knob 66 is fixed, rotation of the yaw adjustment knob 66 causes the relative distance between the two yaw adjustment barrels 92, 94 to vary as the yaw adjustment barrel 94 closer to the yaw adjustment knob 66 moves up and down the screw thread 90.

The structure of the pitch adjustment knob 64 is essentially identical to that of the yaw adjustment knob 66 with the exception of the number of indentations around the periphery of the two knobs with, in this embodiment, the yaw adjustment knob 66 having a greater number of indentations which provides a tactile way of distinguishing between the knobs. Similarly in this embodiment, the roll adjustment knob 60 for controlling the rotary stage 50 is knurled so that it can also be distinguished from the knobs 64, 66 for controlling pitch and yaw.

As with the yaw adjustment knob 66 a screw thread extends from the center of the pitch adjustment knob 64 on which are mounted a pair of barrels (not visible in the Figures), one, remote from the pitch adjustment knob 64 fixed in a fixed position along the screw thread, the other closer to the pitch adjustment knob 64 being free to move along the screw thread. As with the barrels on the screw thread 90 associated with the yaw adjustment knob 66, rotation of the pitch adjustment knob 64 causes the barrel closer to the pitch adjustment knob 64 to move up and down the screw thread while the barrel further from the pitch adjustment knob 64 remains in a fixed location relative to the front of the pitch adjustment knob 64 and therefore rotation of the pitch adjustment knob 64 causes the relative distance between the two barrels mounted on the screw thread to vary.

Returning to FIGS. 4, 5 and 6, the pitch adjustment arm 54 is mounted on the pitch bracket 52 via a pivot which passes through the holes 78 in the upper arms 82 of the U shaped projections 76 extending from the back plate 70 of the pitch bracket 52. This pivot is held in place by a shoulder bolt 95 with a corresponding shoulder bolt 96 being provided at the other end of the pivot. The mounting of the pitch adjustment arm 54 is such that it can rotate about the pivot which allows the end of the pitch adjustment arm 54 remote from the pivot to be moved towards and away from the plane of the back plate 70 of the pitch bracket 52. The barrel attached to the screw thread extending from the pitch adjustment knob 64 remote from the pitch adjustment knob 64 is retained within the holes 80 in the lower arms 84 of the pitch bracket 52 and the recess 86. Similarly the barrel mounted on the screw thread associated with the pitch adjustment knob 64 closer to the pitch adjustment knob 66 is retained within a hole present at the end of the pitch adjustment arm 54 remote from the pivot.

End caps 98, 99 are attached to the ends of the barrels by screws where the diameter of the end caps 98, 99 is slightly greater than the diameter of the barrels. A plastic slip washer 100, 101 is provided between the end caps 98, 99 and the exterior of the pitch bracket 52 and the pitch adjustment arm 54 adjacent the ends of the holes within which the barrels on the screw thread extending from the pitch adjustment knob 64 are mounted. The slip washers 100,101 are held in position by the end caps 98, 99. Further slip washers and end caps are provided on the opposite end of the barrels (not shown in FIGS. 4 and 5). Thus in this way the barrels are mounted within the holes and held within their mounts by the end caps. The mounting of the barrels is such that they are able to rotate within their mountings with the undersides of the end caps 98, 99 moving over the surface of the slip washers 100,101. The effect of enclosing the barrels attached to the screw thread of the pitch adjustment knob 64 within the hole at the end of the pitch adjustment arm 54 and the holes 80 within the lower arms 84 of the pitch bracket 52 is such that as the pitch adjustment knob 64 is rotated and the distance between the barrels mounted on the screw thread of the pitch adjustment knob 64 is caused to be varied this causes the pitch adjustment arm to be rotated about the pivot 95 which alters the pitch of the pitch adjustment arm 54 relative to the back plate 70 of the pitch bracket 52.

The operation of the yaw adjustment of the head plate adjustment assembly 30 is similar to the operation for adjustment of pitch.

In the case of yaw adjustment, an inner yaw adjustment arm 56 is provided and extends from one side of the pitch adjustment arm 54. This inner yaw adjustment arm 56 has a hole of similar dimensions to the holes 80 in the lower arms 84 of the pitch bracket 52 and is arranged to receive the barrel 92 mounted on the screw thread 90 extending from the yaw adjustment knob 66 remote from the yaw adjustment knob 66. The other barrel 94 mounted on the screw thread 90 is then mounted within a similar hole provided at the end of an outer yaw adjustment arm 58. As with the barrels mounted on the screw thread extending from the pitch adjustment knob 64, the barrels 92, 94 mounted on the screw thread 90 extending from the yaw adjustment knob 66 are held in place within their respective holes by end caps 104, 106, 108, 110 attached to the end of the barrels 92, 94. The end caps 104-110 also cause slip washers 112-115 to be retained against the surface of the inner and outer yaw adjustment arms 56, 58 providing a smooth surface against which the undersides of the end caps 104-110 can rest.

In use, rotating the yaw adjustment knob 66 causes the barrel 94 closest to the yaw adjustment knob 66 to move along the screw thread 90. As the location of the other barrel 92 along the screw thread 90 relative to the front of the yaw adjustment knob 66 is fixed, this means that rotating the yaw adjustment knob 66 causes distance between the barrels 92 94 mounted on the screw thread 90 to vary. Since the two barrels 92, 94 are held within cavities at the ends of the inner 56 and outer 58 yaw adjustment arms, this in turn adjusts the separation of the ends of the inner 56 and outer yaw adjustment arms 58 where the barrels 92,94 are held which causes the outer yaw adjustment arm 58 to rotate about the pivot 116 which connects the outer yaw adjustment arm 56 to the pitch bracket 52. This adjusts the orientation of a head plate support 117 extending from the top of the bracket 118 attached to the outer yaw adjustment arm 58 and with it the orientation of the head plate 22 attached to the head plate support 117 via screws passing through screw holes 119 through the head plate support 117.

Adjustment of the roll, pitch and yaw knobs 60, 64, 66 therefore causes variation of roll, pitch and yaw of the head plate 22 relative to the orientation of the base plate 28. The arrangement of the head plate adjustment assembly 30 is such to cause the variation of pitch, yaw and roll of the head plate 22 to originate from a position immediately underneath the plane of the surface of the base plate 28. In the case of the variation in pitch, this is achieved by locating the pivot associated with the pitch bracket 52 within a notch 120 on the underside of the end of the base plate 28. The pivot in the case of adjustment of yaw is arranged to be perpendicular to the pivot for the variation of pitch and is located to intersect the center line of the base plate as indicated by the markings 45. In the case of variation in roll, strictly this arises due to a rotation of the remainder of the head plate adjustment mechanism 30 relative to the rotary stage 50 about an axis parallel to the surface of the base plate 28. However, although the rotation is relative to such an axis, the effect is felt only by virtue of variation of the orientation of the surface of the head plate 22 and hence adjacent to the natural axes of rotation of a patient's neck when the patient is lying on the base plate 28 with their head 26 held next to the head plate 22 by a face mask or invasive head ring.

In addition to providing adjustment of the position of a patient's head which works with the natural range and position of motion available with a patient's neck, the location of the roll, pitch and yaw axes close to the base of a patient's skull also assists with reducing the minor translational errors which arise when rotations are applied. As the axes of rotation do not coincide with the treatment iso-center, it is inevitable that rotations effected by the adjustment of the head plate 22 will introduce minor translational errors. However, these are minimised by the local proximity of the axes of rotation to the base of the skull.

Second Embodiment

A second embodiment of the present invention will now be described. Whereas in the first embodiment a head positioning device 20 was described which enabled the pitch, roll and yaw of a patient's head to be adjusted, in this embodiment a head adjustment device will be described in which in addition to permitting adjustment of the pitch, roll and yaw of a patient's head, also enables fine lateral and vertical adjustments of the position of a patient's head to be made.

Figure 8:
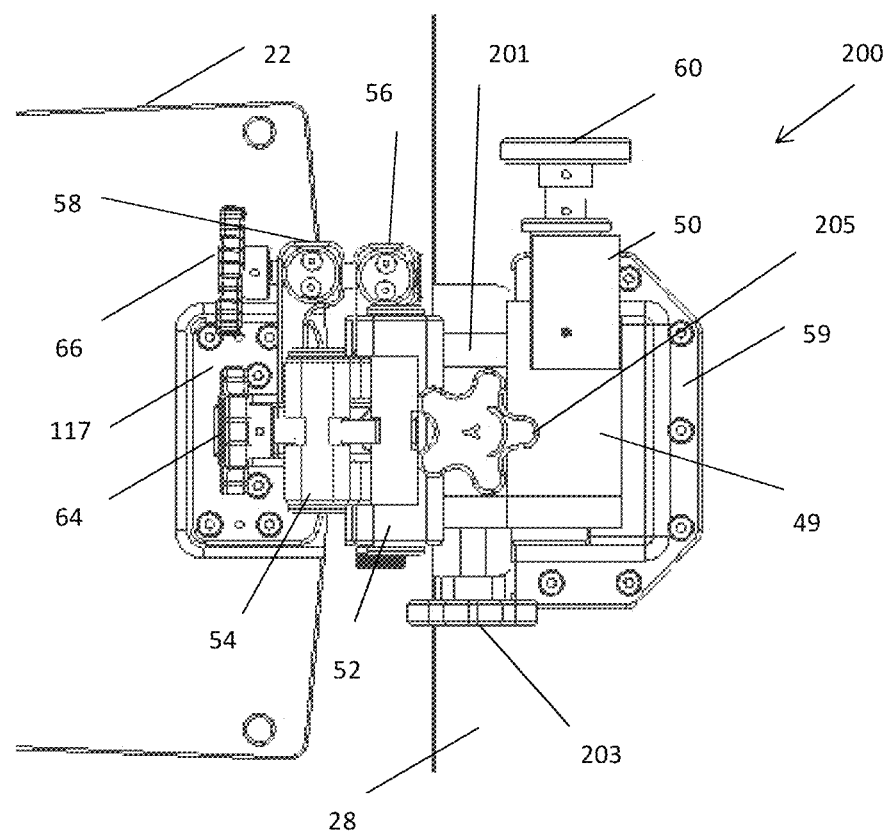
FIG. 8 is an underneath plan view of a head plate adjustment assembly in accordance with a second embodiment of the present invention.

Referring to FIG. 8 which is an underneath plan view of the head plate adjustment assembly 200 suspended beneath and connecting a head plate 22 and a base plate 28. Save as will now be described the head adjustment assembly 200 in this embodiment is identical to the head plate adjustment assembly 30 of the previous embodiment and the reference numbers in FIG. 8 which identify corresponding portions of the head plate adjustment assembly 200 are identified with the same reference numbers as have been used to describe the first embodiment.

The head plate adjustment assembly 200 in this embodiment differs from the head plate adjustment assembly 30 in the first embodiment in that instead of the pitch bracket 52 being attached directly to the rotary stage 50, the pitch bracket is attached to the rotary stage 50 via an X-Y stage 201. In this embodiment, the X-Y stage 201 comprises a pair of dovetail slides which operate under the control of an X adjustment knob 203 and a Y adjustment knob 205. In this embodiment the X adjustment knob 203 is shown as being on the opposite side of the head plate adjustment assembly 200 to the roll adjustment knob 60 and the Y adjustment knob is shown as extending beneath the underside of the head plate adjustment assembly 200. Although in this embodiment the X-Y stage 201 comprises a pair of dovetail slides, it will be appreciated that any suitable form of X-Y stage could be used.

In this embodiment, the X-Y stage 201 is connected to the rotary stage 50 and therefore as the rotary stage is caused to rotate, the X-Y stage is also caused to rotate along with the rest of the head plate adjustment assembly 200. When the X adjustment knob 203 is rotated, this causes the X-Y stage to adjust the lateral position of the pitch bracket 52 relative to the surface of the base plate 28. Similarly, when the Y-adjustment knob 205 is rotated this causes the X-Y stage to adjust the vertical position of the pitch bracket 52 relative to the surface of the base plate 28. The remaining portions of the head plate adjustment mechanism 200 operate in the same manner as has previously been described.

The invention claimed is:

1. A head positioning device comprising:
   a head plate for supporting a patient's head;
   a base plate for connection to a mechanical couch; and
   a head plate adjustment assembly connecting the head plate to the base plate and arranged to vary the relative pitch, yaw and roll of the head plate relative to the base plate, the head plate adjustment assembly including a pitch adjustment mechanism operable to alter the orientation of the head plate about a pitch axis which is substantially located in a plane including the base plate, the pitch adjustment mechanism including:
      a pitch adjustment knob;
      a screw thread extending from the pitch adjustment knob;
      a first and a second barrel mounted on the screw thread;
      a pitch bracket wherein the first barrel mounted on the screw thread is contained within a cavity in the pitch bracket; and
      a pitch adjustment arm pivotably mounted on a pivot on the pitch bracket remote from the first barrel, the second barrel mounted on the screw thread being contained within a cavity in the pitch adjustment arm remote from the pivot.

2. The head positioning device of claim 1, wherein the base plate is operable to be attached to a mechanical couch with the head plate and the head plate adjustment assembly cantilevered off the end of the couch.

3. The head positioning device of claim 2, wherein the head plate adjustment assembly connecting the head plate to the base plate is suspended beneath the head plate and the base plate when the base plate is attached to a mechanical couch with the head plate and the head plate adjustment assembly cantilevered off the end of the couch.

4. The head positioning device of claim 1, wherein the head plate is adapted to secure a patient's head to the head plate.

5. The head positioning device of claim 4, wherein the head plate adjustment assembly is arranged to vary the relative pitch, yaw and roll of the head plate relative to the base plate about axes which intersect at the base of a patient's skull when a patient's head is secured to the head plate.

6. The head positioning device of claim 1, wherein the head plate adjustment assembly includes a rotary stage, the rotary stage being fixed relative to the base plate and operable to alter the orientation of the head plate about a roll axis.

7. A head positioning device, comprising:
   a head plate for supporting a patient's head;
   a base plate for connection to a mechanical couch; and
   a head plate adjustment assembly connecting the head plate to the base plate and arranged to vary the relative pitch, yaw and roll of the head plate relative to the base plate, the head plate adjustment assembly including a yaw adjustment mechanism operable to alter the orientation of the head plate about a yaw axis which is substantially located in a plane perpendicular to the base plate and which lies between the base plate and the head plate, the yaw adjustment mechanism including:
a yaw adjustment knob;
a screw thread extending from the yaw adjustment knob;
a first and a second barrel mounted on the screw thread;
an inner yaw adjustment arm wherein the first barrel mounted on the screw thread is contained within a cavity in the inner yaw adjustment arm; and
an outer yaw adjustment arm pivotably mounted on a pivot on the inner yaw adjustment arm remote from the first barrel, the second barrel mounted on the screw thread being contained within a cavity in the outer yaw adjustment arm remote from the pivot.

8. The head positioning device of claim 7, wherein the head plate adjustment assembly comprises:
a rotary stage;
a pitch adjustment assembly; wherein the head plate is connected to the base plate via the rotary stage, the pitch adjustment assembly, and the yaw adjustment assembly.

9. The head positioning device of claim 8, wherein the pitch adjustment mechanism comprises:
a pitch adjustment knob;
a screw thread extending from the pitch adjustment knob;
a first and a second barrel mounted on the screw thread;
a pitch bracket wherein the first barrel mounted on the screw thread is contained within a cavity in the pitch bracket; and
a pitch adjustment arm pivotably mounted on a pivot on the pitch bracket remote from the first barrel, the second barrel mounted on the screw thread being contained within a cavity in the pitch adjustment arm remote from the pivot.

10. The head plate positioning device of claim 7, wherein the head plate adjustment assembly further comprises an X-Y stage and the head plate adjustment assembly is arranged to vary the relative height and lateral position of the head plate relative to the base plate.

* * * * *